US008039265B1

(12) United States Patent
Cai et al.

(10) Patent No.: US 8,039,265 B1
(45) Date of Patent: Oct. 18, 2011

(54) DETERMINING OXYGEN CONTENT OF METAL SPECIES IN HETEROGENEOUS CATALYSTS

(75) Inventors: Juan Cai, Fremont, CA (US); Kyle L. Fujdala, San Jose, CA (US); Mats I. Larsson, Sunnyvale, CA (US)

(73) Assignee: Nanostellar, Inc., Redwood City, CA (US)

( * ) Notice: Subject to any disclaimer, the term of this patent is extended or adjusted under 35 U.S.C. 154(b) by 741 days.

(21) Appl. No.: 12/050,062

(22) Filed: Mar. 17, 2008

(51) Int. Cl.
*G01N 33/00* (2006.01)
(52) U.S. Cl. .......................... 436/138; 436/37
(58) Field of Classification Search .................. 436/37, 436/138
See application file for complete search history.

(56) References Cited

U.S. PATENT DOCUMENTS

| | | | | |
|---|---|---|---|---|
| 4,729,824 | A * | 3/1988 | Giner | 204/415 |
| 5,436,165 | A * | 7/1995 | Brenner | 436/149 |
| 6,306,349 | B1 * | 10/2001 | Moon et al. | 422/69 |

OTHER PUBLICATIONS

Gruber, Hans, "Chemisorption Studies on Supported Platinum", The Journal of Physical Chemistry 1962 66 (1), 48-54.*
Brooks et al., "Chemisorption of carbon monoxide on metal surfaces by pulse chromatography", Analytical Chemistry 1969 41 (1), 103-106.*
Hoang-Van et al., "Hydrogen-Oxygen Titration and Carbon Monoxide Chemisorptiopn for the Measurement of Supported Palladium Surface Areas", React. Kinet. Catal. Lett., vol. 13, No. 1, 63-67 (1980).*
Szymura, "Effects of Reduction Temperature on H2 Adsorption by Pt on Various Supports", Strong Metal-Support Interactions. Feb. 10, 1986, 169-181.*
Bergeret, G. et al., "Metal Particle Size and Dispersion Measurements," *Handbook of Heterogeneous Catalysis*, vol. 2, pp. 439-442, Wiley-VCH (1997).
Morlang, A, et al., "Bimetallic Pt/Pd Diesel Oxidation Catalysts—Structural Characterisation and Catalytic Behaviour," *Applied Catalysis B: Environmental 60*, pp. 191-199 (2005).
Baraldi, A., "Real-time X-ray Photoelectron Spectroscopy of Surface Reactions," *Surface Science Report 49*, pp. 169-224 (2003).
Hansen, E. et al., "First-Principles Based Kinetic Simulations of Acetic Acid Temperature Programmed Reaction on Pd(111)," J. Phys. Chem. B, 105, pp. 9218-9229 (2001).
Meier, Mike, "Crystallite Size Measurement Using X-Ray Diffraction," Department of Chemical Engineering and Materials Science, University of California, Davis, Sep. 13, 2004, pp. 1-6.
Webb, Paul A., "Introduction to Chemical Adsorption Analytical Techniques and their Application to Catalysis," Micromeritics Instrument Corp./MIC Technical Publications, Jan. 2003, pp. 1-12.
Micromeritics Product Brochure, "ChemiSorb Series—Chemisorption Analyzers," http://www.micromeritics.com/pdf/products/ChemiSorb_Brochure.pdf, pp. 1-8, (2004).

(Continued)

*Primary Examiner* — Jill Warden
*Assistant Examiner* — Monique Cole
(74) *Attorney, Agent, or Firm* — Patterson & Sheridan, LLP (57) ABSTRACT

The oxygen content of metal species in a heterogeneous catalyst is determined using volumetric adsorption measurements. Such measurements are employed to quantify the amount of reduction gas that it takes to reduce metal species of a catalyst sample, and the oxygen content is derived from this amount and the reaction stoichiometry. This method can be applied to mono-metallic and multi-metallic heterogeneous catalysts and has been shown to provide at least 10 times better detection sensitivity than typical TCDs in TPR-TCD methods.

31 Claims, 4 Drawing Sheets

OTHER PUBLICATIONS

Lassi, Ulla, "Deactivation Correlations of PD/RH Three-Way Catalysts Designed for EURO IV Emission Limits," University of Oulu Press (dissertation), Feb. 28, 2003, pp. 1-136.

Tsud, N. et al., "CO Adsorption on Palladium Model Catalysts: XPS Pd—$Al_2O_3$ Interaction Study," Surface Science 467, pp. 169-176 (2000).

Wertheim, G. K. et al., "Noble and Transition-Metal Clusters: The D Bands of Silver and Palladium," PhysicalReview B, vol. 33(8), pp. 5384-5390 (1986).

Ottens, A. K. et al., "Real-Time Quantitative Analysis of $H_2$, He, $O_2$ and Ar by Quadrupole Ion Trap Mass Spectrometry", J. Am. Soc. Mass Spectrom 13, pp. 1120-1128 (2002).

Graham, J. D. et al., "Interaction of Hydrogen Chloride with an Ultrathin Ice Film: Observation of Adsorbed and Absorbed States," J. Phys. Chem., 98, pp. 5974-5983 (1994).

Wang, C-B et al., "Effects of the Addition of Titania on the Thermal Characterization of Alumina-supported Palladium", Journal of Molecular Catalysis A: Chemical 180, pp. 285-291 (2002).

Patnaik, P., "Dean's Analytical Chemistry Handbook," 2nd Edition, McGraw Hill Companies 2004, p. 5.47.

Lowell, S. et al. "Characterization of Porous Solids and Powders: Surface Area, Pore Size and Density," Chapter 16, pp. 283-296, Kluwer Academic Publishers, 2004.

Ragaini, V. et al., "Dispersion Measurement by the Single Introduction Method Coupled With the Back-Sorption Procedure: A Chemisorption and TPD Study of the Different Chemisorbed Hydrogen Species," Journal of Catalysis 146, pp. 116-125 (1994).

Benson, J. E. et al., "Hydrogen-Oxygen Titration Method for the Measurement of Supported Palladium Surface Areas," Journal of Catalysis 30, pp. 146-153 (1973).

Leon y Leon, C. A. et al., "Adsorption and Catalytic Properties of $Pd/SiO_2$, $Cu/SiO_2$ and $Pd-Cu/SiO_2$ Systems—I. Hydrogen, Carbon Monoxide and Oxygen Adsorption on $Pd/SiO_2$ and $Cu/SiO_2$," Applied Catalysis 69, pp. 269-290 (1991).

Chafik, T. et al., "Heat of Adsorption of Carbon Monoxide on a $Pt/Rh/CeO_2/Al_2O_3$ Three-Way Catalyst Using In-Situ Infrared Spectroscopy At High Temperatures," Journal of Catalysis 179, pp. 503-514 (1998).

Dropsch, H. et al., "CO Adsorption on Supported Pd Catalysts Studied by Adsorption Microcalorimetry and Temperature Programmed Desorption", Applied Catalysis A: General 158, pp. 163-183 (1997).

\* cited by examiner

DETERMINING OXYGEN CONTENT OF METAL SPECIES IN HETEROGENEOUS CATALYSTS

BACKGROUND OF THE INVENTION

1. Field of the Invention

The present invention generally relates to catalyst characterization and, more particularly, to determining the oxygen content of metal species in a heterogeneous catalyst.

2. Description of the Related Art

The performance of catalysts is highly dependent on their physical and chemical properties. However, it is often difficult to directly measure physical and chemical properties of supported metal species in catalysts, especially when the metal species are well dispersed. Catalyst developers therefore rely on sophisticated characterization techniques to determine the physical and chemical properties and performance characteristics of new catalyst designs.

One property that influences the performance of catalysts is the oxidation states of the catalyst metal species, as it is well understood that the catalytic activity of a metal is different from that of the same metal that is oxidized. Metal species in a heterogeneous catalyst can become oxidized during catalyst synthesis and/or processing. Various methods have been employed in the art to determine the oxygen content of metal species in a heterogeneous catalyst. The routine methods include X-ray photoelectron spectroscopy (XPS) and temperature programmed reduction (TPR).

XPS is also known as ESCA (Electron Spectroscopy for Chemical Analysis). It is a technique that measures the binding energies of the electrons in the atoms (a function of the type of atom and its environment) on a material surface. XPS spectra are obtained by irradiating a material with a beam of X-rays while simultaneously measuring the kinetic energy and the number of electrons that escape from the top 1 to 10 nm of the material being analyzed. Because the binding energies of the electrons in an atom depend on the chemical status (i.e., ionic or metallic), the binding energy spectra obtained from XPS can be used to derive the oxidation states of the targeted elements.

There are some limitations with XPS. One is the detection limit. It is difficult to obtain high quality XPS spectra in samples with low metal loadings, because the detection limit of XPS is typically >0.5 atomic percent (0.5 at %). For example, in a heterogeneous catalyst having palladium metal particles supported on alumina with a metal loading of 1 weight percent (1 wt %), the atomic loading of palladium is 0.2 at %, far below the detection limit of XPS. It would be very difficult to get high quality XPS spectra in such samples.

The XPS energy resolution is another limitation. In general, the energy resolution of an XPS instrument is ~0.5 eV. However, the real XPS peak width depends on sample conditions. The peak width usually becomes broad for very small particles. The increased peak width is not desirable because it reduces the ability to distinguish the ionic state of targeted species, especially when the binding energy difference between ionic states is small. For example, the peak width in the case of small palladium particles can be as large as 2 eV, while the binding energy difference between the palladium metal ($Pd^0$) and the $Pd^{2+}$ ion is 1.2 eV. In this situation, it would be very difficult to identify the chemical state of palladium.

In TPR measurements, a certain amount of catalyst is loaded into a flow reactor. A gas mixture of hydrogen (or another reduction gas) in argon (or another inert gas) flows through the catalyst sample as the sample is heated from a low temperature to a higher temperature. The amount of reduction gas uptake during this process is measured and the amount of oxide is calculated based on the reduction stoichiometry. Various detectors can be used to measure the reduction gas uptake but thermal conductivity detector (TCD) is most often used.

Although TCDs are the most universal detectors available, it is well known that they are not very sensitive. A number of factors influence the detection limit of a TCD. The breadth of a given TCD peak is directly affected by the reduction kinetics. In general, for broad TPR peaks, the detection limit is ~50 µmol of reduction gas. For sharp peaks, the detection limit can be as low as 10 µmol. As a way to increase the accuracy of data when using TCD in TPR, the amount of sample may need to be increased to boost the reduction gas consumption.

SUMMARY OF THE INVENTION

The present invention provides an alternative method for determining the oxygen content of metal species in a heterogeneous catalyst. According to embodiments of the present invention, volumetric adsorption is employed to quantify the amount of reduction gas that it takes to reduce the oxidized metal species in a catalyst sample. The oxygen content of the metal species is derived from this amount and the reaction stoichiometry. This method can be applied to mono-metallic and multi-metallic heterogeneous catalysts.

The invention takes advantage of the high detection sensitivity of volumetric adsorption systems in measuring the adsorbed gas volume. The detection limit of a volumetric adsorption system can be as low as 1 µmol of gas. Therefore, the present invention provides at least 10 times better sensitivity than typical TCDs in measuring the amount of gas consumed during the reduction process.

The method for determining the oxygen content of metal species in a catalyst sample, according to embodiments of the invention, includes several steps. The first step is to perform volumetric measurements on a fresh sample using a reduction gas to determine the amount of the reduction gas that is chemically consumed by the metal species in the sample. The second step is to measure the amount of gas that is chemically adsorbed on the metal species in the sample using one of several approaches. One approach is to heat the sample to remove the chemically adsorbed gas on the surface of the metal species and perform volumetric adsorption measurements using an adsorbate gas. Other approaches include conventional pulse chemisorption measurements on fresh samples that have been treated to reduce the metal species in the sample. The oxygen content of the metal species in the sample can be determined based on the amount of the reduction gas that has been chemically consumed by the metal species in the sample and the amount of the adsorbate gas that has been chemically adsorbed onto the metal species in the treated sample.

The reduction gas may be $H_2$ or CO and the adsorbate gas may be $H_2$, CO, $O_2$ or NO, and they may be the same or different. Further, the heterogeneous catalyst may contain one or more metal species. If the heterogeneous catalyst contains more than one metal species, a range of possible oxygen content of the metal species in the sample is determined based on the possible adsorbate-metal stoichiometries.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Embodiments of the present invention provide a method for determining the oxygen content of metal species in a heterogeneous catalyst that contain one or more metal species. In this method, volumetric adsorption measurements are employed to quantify the amount of reduction gas that it takes to reduce the oxidized metal species in a catalyst sample, and the oxygen content of the metal species is derived from this amount and the reaction stoichiometry.

Figure 1:
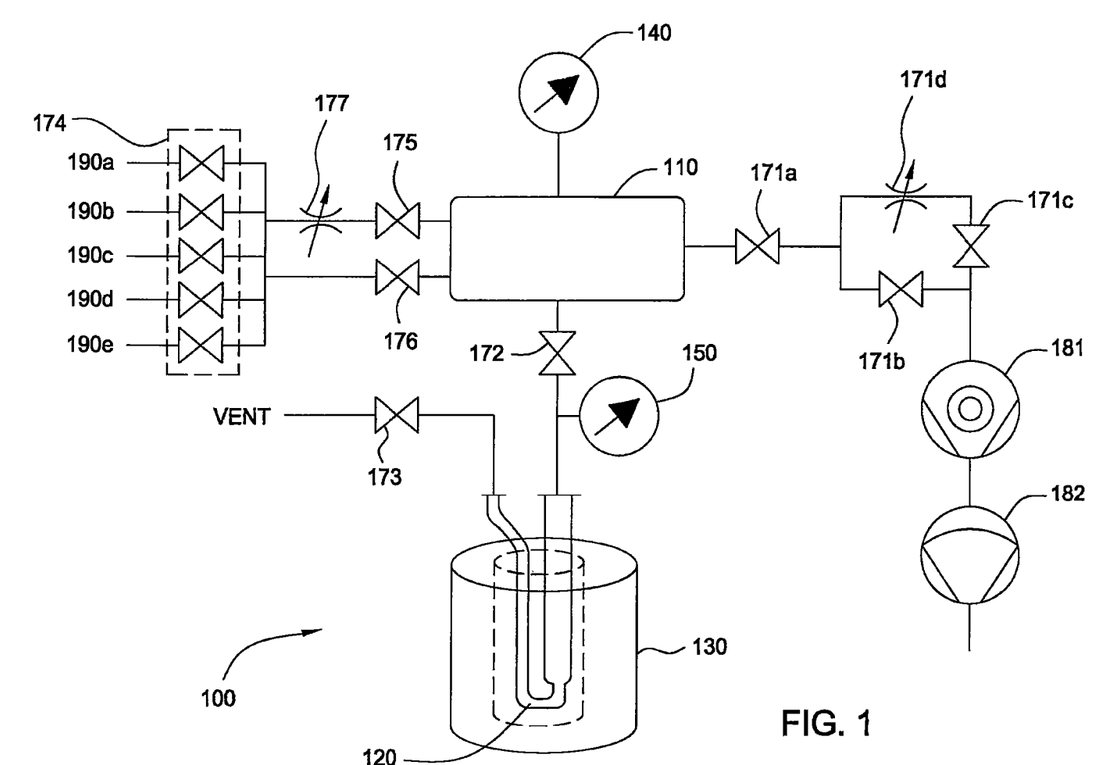
FIG. 1 is a diagram of a volumetric adsorption system that can be employed to carry out the embodiments of the present invention.

FIG. 1 is a diagram of a volumetric adsorption system that can be employed to carry out the embodiments of the present invention. One example of such a system is Autosorb-1C, which is commercially available from Quantachrome Corporation. The system 100 includes a fixed volume manifold 110 from which probe gas is dosed into a flow-through sample cell 120. The flow-through sample cell 120 contains the catalyst sample (not shown) and is housed in a furnace 130 for heating the catalyst sample. A first pressure transducer 140 is provided for measuring the pressure of the manifold 110 and a second pressure transducer 150 is provided for measuring the pressure of the flow-through sample cell 120. In general, pressure transducers used in the system cover a wide pressure range. A pressure transducer with approximately 1000 Torr full scale having an accuracy of ±0.1% is employed to measure the pressure range from 100 mmHg to 1 atmosphere. A 10 and/or 1 Torr full scale pressure transducer having an accuracy of ±0.15% is commonly utilized to cover the lower pressure range. The pressure of the manifold 110 and the flow-through sample cell 120 is controlled by operating valves 171a, 171b, 171c, 171d, 172, 173 and a pair of pumps, which include a turbo-molecular pump 181 and a diaphragm pump 182. Probe gas is supplied into the manifold 110 through one or more of supply lines 190a-190e, each connected to a different gas source (not shown). Valves 174, 175, 176, 177 control the selection and the flow rate of the probe gas supplied into the manifold 110.

Figure 2:
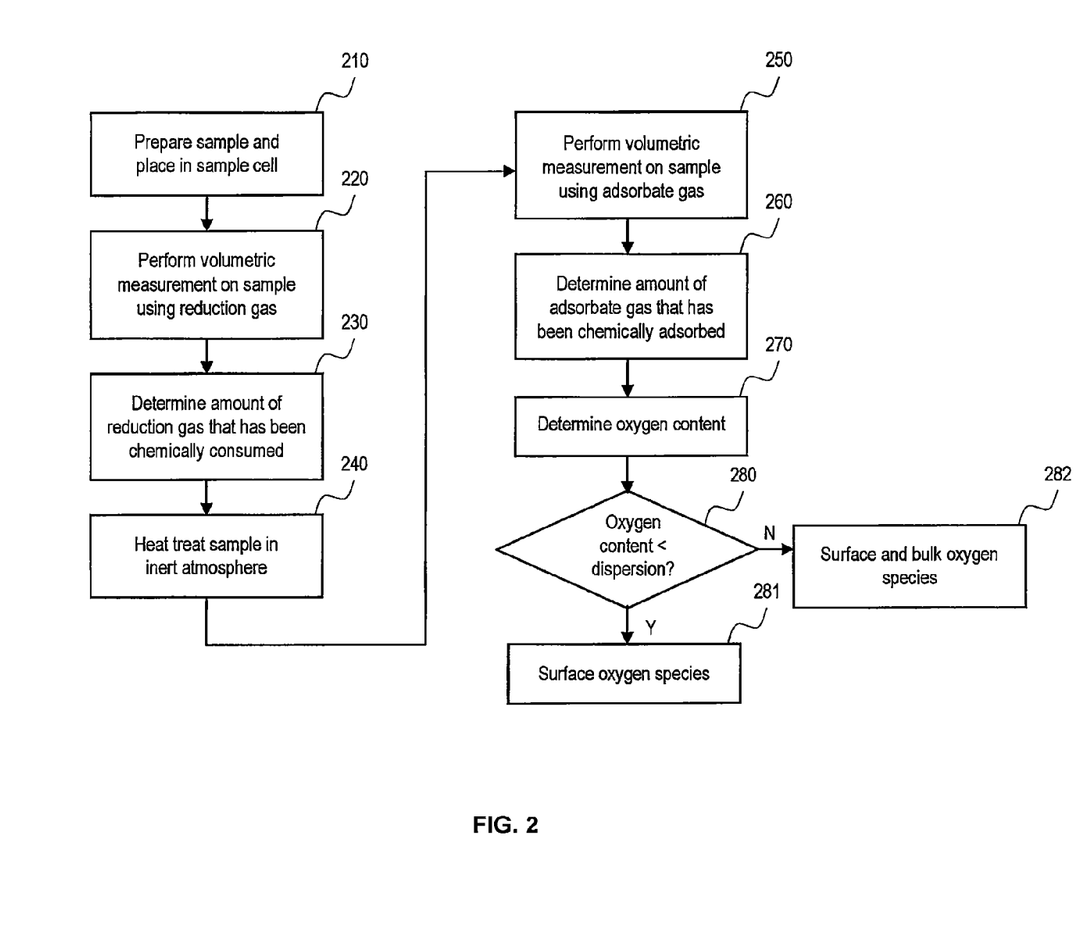
FIG. 2 is a flow diagram illustrating a method for determining the oxygen content of metal species in a heterogeneous catalyst.

FIG. 2 is a flow diagram illustrating the method for determining the oxygen content of metal species in a heterogeneous catalyst. In step 210, a heterogeneous catalyst sample is prepared and placed into the sample cell 120. Then, a first volumetric adsorption measurement using a reduction gas is performed on the sample in step 220. Based on the measurements taken in step 220, the amount of reduction gas that has been chemically consumed ($N_{chem}$) is determined in step 230. The amount of reduction gas that is chemically consumed includes the amount of reduction gas that is taken or removed from the system by virtue of its reacting with oxygen and being chemically adsorbed (chemisorbed) on the surface of the sample. In step 240, the sample is heated within the sample cell 120 in inert atmosphere to a temperature of 200° C. for 60 minutes to remove the adsorbed reduction gas in the sample. Then, a second volumetric adsorption measurement using an adsorbate gas is performed on the sample in step 250. Based on the measurements taken in step 250, the amount of adsorbate gas that has been chemically adsorbed ($N_{ads}$) is determined in step 260.

In step 270, the oxygen content of metal species in the sample is determined as $y*N_{chem}$ where y represents the fraction of $N_{chem}$ that is used for reduction and (1−y) represents the fraction of $N_{chem}$ that has been chemically adsorbed. Therefore, $(1-y)*N_{chem}$ represents the moles of reduction gas that have been chemically adsorbed, and this value should equal $N_{ads}$ if the reduction gas used in step 220 and the adsorbate gas used in step 250 are the same. Therefore, in the case where the reduction gas used in step 220 and the adsorbate gas used in step 250 are the same: $(1-y)*N_{chem}=N_{ads}$ or $y=1-N_{ads}/N_{chem}$. In the case where the reduction gas used in step 220 and the adsorbate gas used in step 250 are not the same, the expression for y is derived using the general expression for dispersion in the following manner. The metal dispersion in heterogeneous catalysts is defined as the ratio between the number of surface metal atoms ($M_{surf}$) and the number of total metal atoms ($M_{total}$). The number of surface metal atoms can be determined from $N_{ads}$ or $(1-y)*N_{chem}$, as long as the chemisorption bonding stoichiometry (θ) between the probe gas and the metal surface atom is known. θ represents the number of chemically adsorbed gas molecules bonded to a unit surface metal atom. Therefore, the following relationships can be obtained:

$$\text{Disperion} = \frac{M_{surf}}{M_{total}} = \frac{(1-y)*N_{chem}(\text{reduction\_gas})}{\theta(\text{reduction\_gas}) \cdot M_{total}} = \frac{N_{ads}(\text{adsorbate\_gas})}{\theta(\text{adsorbate\_gas}) \cdot M_{total}}$$

$$y = 1 - \frac{\theta(\text{reduction\_gas}) N_{ads}(\text{adsorbate\_gas})}{\theta(\text{adsorbate\_gas}) N_{chem}(\text{reduction\_gas})} = 1 - \mu \frac{N_{ads}(\text{adsorbate\_gas})}{N_{chem}(\text{reduction\_gas})}$$

where μ=(θ of the reduction gas)/(θ of the adsorbate gas). θ of the reduction gas means the bonding stoichiometry between the reduction gas molecule and the surface metal atom, and θ of the adsorbate gas means the bonding stoichiometry between the adsorbate gas molecule and the surface atom. For example, if $H_2$ is used as the reduction gas and CO is used as the adsorbate gas to study platinum species in the catalysts, the expression for y is:

$$y = 1 - \mu \frac{N_{ads}(CO)}{N_{chem}(H)} = 1 - \mu \frac{N_{ads}(CO)}{2*N_{chem}(H_2)},$$

where $\mu=(\theta_H/\theta_{CO})$. $H_2$ molecule is dissociated into H atoms to bond to metal surfaces in the chemisorption process (i.e., $N_{chem}(H)=2N_{chem}(H_2)$), and CO molecule bonds directly to the metal surface atoms in this case.

θ may be known, determined experimentally, e.g., using infrared spectroscopy or time-resolved X-ray photo-electron spectroscopy, as described in A. Baraldi, et al., "Real-time X-ray Photoelectron Spectroscopy of Surface Reactions," Surface Science Report 49, 169 (2003), or determined by computational modeling, e.g., using density functional theory combined with kinetic Monte Carlo simulations as described in E. Hansen and M. Neurock, "First-Principles Based Kinetic Simulations of Acetic Acid Temperature Programmed Reaction on Pd(111)," J. Phys. Chem. B, 105, 9218 (2001). For some metals and probe gases, the range of $\theta$ is well known to those skilled in the art. Some typical $\theta$ values are commonly used by practitioners in the field to determine the metal dispersions in catalysts. The following table provides some metals and probe gases for which the typical $\theta$ is listed.

| Probe Gas | Metal | $\theta$ |
|---|---|---|
| H | Pt | 1 |
| H | Pd | 1 |
| CO | Pt | 1 |
| CO | Pd | 0.5 |

In step 280, the amount of oxygen is determined as a percentage of metal in the heterogeneous catalyst sample and compared against the metal dispersion. If the amount of oxygen determined as a percentage of metal is less than the metal dispersion, this suggests that oxygen likely exists only as surface species (step 281). On the other hand, if the amount of oxygen determined is larger than the metal dispersion, this suggests that oxygen may exist not only as surface species but are also as a form of oxidized metal species (step 282).

Figure 3:
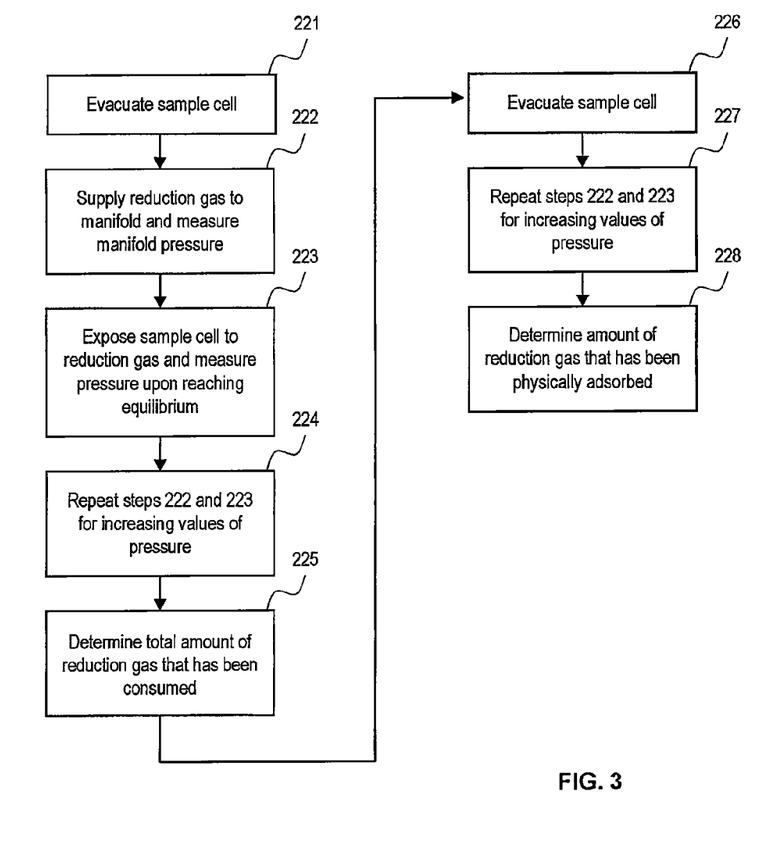
FIG. 3 is a flow diagram illustrating a first volumetric adsorption step employed in the method of FIG. 2.

FIG. 3 is a flow diagram illustrating the first volumetric measurement step, step 220, employed in the method of FIG. 2. In step 221, the sample cell 120 containing the heterogeneous catalyst sample is evacuated to near vacuum using the pumps 181, 182 until the outgas rate is less than a threshold value.

In step 222, reduction gas is supplied into the manifold 110 through one of the supply lines 190a-e by operating valves 174, 175, 176, 177. Valve 172 remains closed throughout this step, so the volume into which the reduction gas is introduced, $V_0$, is the volume of the manifold 110, which is a fixed value. The pressure of the manifold, $P_0$, is measured using the pressure transducer 140, and when the manifold 110 reaches a predetermined pressure, the supply of reduction gas is stopped. The reduction gas can be $H_2$ or CO. Valves 175, 176 are closed after this step. In step 223, valve 172 is opened. As a result, the reduction gas in the manifold 110 flows into the sample cell 120 and begins adsorbing onto the surface of the metal species in the sample as well as reducing the oxygen atoms of the metal species. Pressure drop of the combined manifold-cell system is observed from: (1) reaction of the reduction gas with oxygen content in the metal species; and (2) adsorption of reduction gas onto the surface of the metal species. When equilibrium is reached, the pressure of the manifold-cell system, $P_1$, is measured using the pressure transducer 150.

Steps 222 and 223 are then repeated for increasing values of $P_1$ (step 224). The measured values of $P_0$ and $P_1$ and the fixed values of $V_0$ and $V_1$ (where $V_1$ represents the combined volume of the manifold 110 and the sample cell 120) are used to determine the total number of moles of reduction gas that have been consumed by the sample at each value of $P_1$ based on the ideal gas equation: n=PV/RT (step 225), where n is the amount of gas in moles, P is the gas pressure, V is the gas volume, T is the gas temperature, and R is the ideal gas constant 8.3145 J/(mol K). It is preferable to maintain the temperature of the manifold 110 and the sample cell 120 at a constant value (e.g. 25° C. or room temperature), during each of the steps 222-224. The temperatures within the manifold 110 and the manifold-cell system are nonetheless monitored during steps 222-224, and any variations in the temperature are accounted for when using the equation: n=PV/RT.

The total amount of gas consumed, as determined in step 225, includes gas consumed by the reduction reaction, chemically (strongly) adsorbed gas, and physically (weakly) adsorbed gas. Steps 226-228 are carried out to determine the amount of reduction gas that is physically adsorbed, so that the amount of reduction gas that is chemically consumed can be determined.

In step 226, the sample cell 120 containing the heterogeneous catalyst sample is evacuated to near vacuum (e.g. P<0.005 torr) using the pumps 181, 182 at room temperature. As a result, the chemically adsorbed reduction gas molecules remain adsorbed onto the surface of the metal species, while the physically adsorbed reduction gas molecules are desorbed from the surface of the metal species and evacuated.

Then, steps 222 and 223 are carried out for increasing pressure values of $P_0'$ and $P_1'$, where $P_0'$ represents the pressure of the manifold 110 and $P_1'$ represents the pressure of the combined manifold-cell system (step 227). The measured values of $P_0'$ and $P_1'$ and the fixed values of $V_0$ and $V_1$ are used to determine the number of moles of reduction gas that are physically adsorbed onto the metal species at each $P_1'$ using the equation: n=PV/RT (step 228). It is preferable to maintain the temperature of the manifold 110 and the sample cell 120 at a constant value (e.g., 25° C. or room temperature), during step 227. The temperatures within the manifold 110 and the manifold-cell system are, however, monitored during step 227, and any variations in the temperature are accounted for when using the equation: n=PV/RT. Subtraction of the number of moles of reduction gas that are physically adsorbed from the total number of moles of reduction gas that are consumed gives the number of moles of reduction gas that are chemically consumed (step 230 of FIG. 2).

Figure 4:
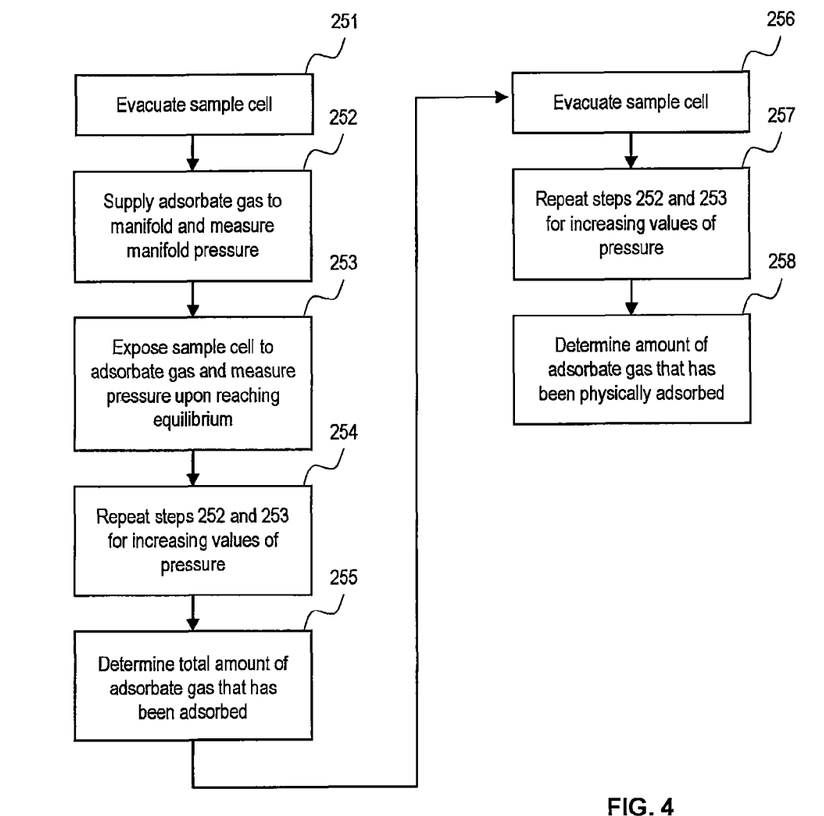
FIG. 4 is a flow diagram illustrating a second volumetric adsorption step employed in the method of FIG. 2.

FIG. 4 is a flow diagram illustrating a second volumetric adsorption step, step 250, employed in the method of FIG. 2. In step 251, the sample cell 120 containing the heterogeneous catalyst sample is evacuated to near vacuum using the pumps 181, 182 until the outgas rate is less than a threshold value.

In step 252, adsorbate gas is supplied into the manifold 110 through one of the supply lines 190a-e by operating valves 174, 175, 176, 177. Valve 172 remains closed throughout this step, so the volume into which the reduction gas is introduced, $V_0$, is the volume of the manifold 110, which is a fixed value. The pressure of the manifold, $P_0$, is measured using the pressure transducer 140, and when the manifold 110 reaches a predetermined pressure, the supply of reduction gas is stopped. The adsorbate gas can be any of $H_2$, CO, $O_2$ and NO. Valves 175, 176 are closed after this step. In step 253, valve 172 is opened. As a result, the adsorbate gas in the manifold 110 flows into the sample cell 120 and begins adsorbing onto the surface of the metal species in the sample. Pressure drop of the combined manifold-cell system is observed from the adsorption of adsorbate gas molecules onto the surface of the metal species. When equilibrium is reached, the pressure of the manifold-cell system, $P_1$, is measured using the pressure transducer 150.

Steps 252 and 253 are then repeated for increasing values of $P_1$ (step 254). The measured values of $P_0$ and $P_1$ and the fixed values of $V_0$ and $V_1$ (where $V_1$ represents the combined volume of the manifold 110 and the sample cell 120) are used to determine the total number of moles of adsorbate gas that have been adsorbed onto the surface of the metal species at each value of $P_1$ based on the equation: n=PV/RT (step 255). It is preferable to maintain the temperature of the manifold 110 and the sample cell 120 at a constant value (e.g., 25° C. or room temperature), during each of the steps 252-254. The temperatures within the manifold 110 and the manifold-cell system are, however, monitored during steps 252-254, and any variations in the temperature are accounted for when using the equation: n=PV/RT.

The total number of moles of gas adsorbed, as determined in step 255, includes those that are chemically adsorbed, and those that are physically adsorbed. In step 256, the sample cell 120 containing the heterogeneous catalyst sample is evacuated to near vacuum using the pumps 181, 182 at room temperature. As a result, the chemically adsorbed adsorbate gas molecules remain adsorbed onto the surface of the metal species, while the physically adsorbed adsorbate gas molecules are desorbed from the surface of the metal species and evacuated.

Then, steps 252 and 253 are carried out for increasing pressure values of $P_0'$ and $P_1'$, where $P_0'$ represents the pressure of the manifold 110 and $P_1'$ represents the pressure of the combined manifold-cell system (step 257). The measured values of $P_0'$ and $P_1'$ and the fixed values of $V_0$ and $V_1$ are used to determine the number of moles of adsorbate gas that are physically adsorbed onto the metal species at each $P_1'$ using the equation: n=PV/RT (step 258). It is preferable to maintain the temperature of the manifold 110 and the sample cell 120 at a constant value (e.g., 25° C. or room temperature), during step 257. The temperatures within the manifold 110 and the manifold-cell system are, however, monitored during step 257, and any variations in the temperature are accounted for when using the equation: n=PV/RT. Subtraction of the number of moles of adsorbate gas that are physically adsorbed from the total number of moles of adsorbate gas that are adsorbed gives the number of moles of adsorbate gas that are chemically adsorbed (step 260 of FIG. 2).

As an alternative to steps 251-258, the number of moles of gas that are chemically adsorbed may be determined using a different chemisorption measurement technique, including pulse adsorption, which is well known to those skilled in the art.

The following examples serve to explain and illustrate the method for determining oxygen content of metal species according to various embodiments of the present invention. In the following examples, the metal loading of platinum or palladium is determined from elemental analysis methods such as DCP-OES, atomic adsorption or XRF.

Example 1

In this example, the sample is 0.193 g of a platinum catalyst supported on alumina with a metal loading of 3.3 wt % (Pt=153.77 μmol/g). Steps 220 and 230 are carried out using $H_2$ as the reduction gas and $N_{chem}(H_2)$ is determined to be 113.85 μmol/g. $N_{ads}(CO)$=99.94 μmol/g is determined separately using pulse adsorption, giving a dispersion of 0.65. Using the formulation for y derived above and μ=1, y=0.56 and the oxygen content is $y*N_{chem}(H_2)$ or 63.76 μmol/g. The oxygen concentration, O/Pt, is 41 at % and this is less than the dispersion of 0.65. This would suggest that the oxygen exists as surface species only.

Example 2

In this example, the sample is 0.215 g of a platinum catalyst supported on alumina with a metal loading of 6.0 wt % (Pt=292.16 μmol/g). Steps 220 and 230 are carried out using $H_2$ as the reduction gas and $N_{chem}(H_2)$ of 157.08 μmol/g is determined. $N_{ads}(CO)$=121.8 μmol/g is determined separately using pulse adsorption, giving a dispersion of 0.42. Using μ=1 for platinum and the formulation for y derived above, y=0.61 and the oxygen content is $y*N_{chem}(H_2)$ or 95.82 μmol/g. The oxygen concentration, O/Pt, is 33 at % and this is less than the dispersion of 0.42. This would suggest that the oxygen exists as surface species only.

Example 3

In this example, the sample from Example 2 after step 230 ($N_{chem}(H_2)$=157.08 μmol/g) is further treated by heating and carrying out steps 250 and 260 using $H_2$ as the adsorbate gas. $N_{ads}(H_2)$ of 72.3 μmol/g is determined, giving a dispersion of 0.49. Using the formulation for y derived above and μ=1, y=0.54 and the oxygen content is $y*N_{chem}(H_2)$ or 84.82 μmol/g. The oxygen concentration, O/Pt, is 29 at % and this is less than the dispersion of 0.49. This would suggest that the oxygen exists as surface species only.

Example 4

In this example, the sample is 0.183 g of a palladium catalyst supported on alumina with a metal loading of 3.0 wt % (Pd=281.95 μmol/g). Steps 220 and 230 are carried out using $H_2$ as the reduction gas and $N_{chem}(H_2)$ of 328.50 μmol/g is determined. Physically absorbed H species in the form of palladium hydride are not included $N_{chem}(H_2)$, since they can be easily removed by evacuation (step 226). $N_{ads}(CO)$ of 76.13 μmol/g is determined separately using pulse adsorption. Using μ=2 for palladium and so using the formulation for y derived above, y=0.77 and the oxygen content is $y*N_{chem}(H_2)$ or 252.95 μmol/g. The oxygen concentration, O/Pd, is 90 at % and this is greater than the dispersion of 0.54. Since PdO is known to be the stable oxide form in Pd/alumina systems, the measurement would suggest that 90% of Pd in the starting sample is oxidized.

Example 5

In this example 0.331 g of the sample in Example 1 and 0.665 g of the sample in Example 4 are mixed together to obtain a uniform sample with a metal loading of 2.0 wt % Pt (Pt=102.51 μmol/g) and 1.0 wt % Pd (Pd=93.98 μmol/g). The nominal atomic composition of this sample is $Pt_{50}Pd_{50}$. A 0.183 g portion of the mixture is taken, and steps 220 and 230 are carried out using $H_2$ as the reduction gas, giving $N_{chem}(H_2)$ of 181.90 μmol/g. $N_{ads}(CO)$ of 109.25 μmol/g is determined separately using pulse adsorption. $\theta_H$ for this sample is 1 because the typical $\theta_H$ for both Pt and Pd are 1, and that $\theta_{CO}$ for this sample is between $\theta_{CO}$ for Pt (1) and $\theta_{CO}$ for Pd (2). It is reasonable to assume that $\theta_{CO}$ for this physically mixed PtPd sample follows a linear relationship with the relative composition of Pt and Pd, and so $\theta_{CO}$ for $Pt_{50}Pd_{50}$ is 1.3. Using the formulation for y derived above, y=0.61 and the oxygen content is $y*N_{chem}(H_2)$ or 110.96 μmol/g. The oxygen concentration, O/(Pt+Pd), is 56 at %. Since the oxygen content in the materials from Examples 1 and 4 is known, the $O/(Pt_+Pd)$ value in the sample can be easily calculated. The oxygen concentration from the Pt component (Example 1) is 102.51 μmol/g×0.41, and that from the Pd component (Example 4) is 93.98 μmol/g×0.90. Therefore, the oxygen content in this mixed sample should be (102.51 μmol/g×0.41+ 93.98 μmol/g×0.90)/(102.51 μmol/g+93.98 μmol/g)=64 at %. Thus, the measured value (56 at %) is quite close to what it is expected (64 at %).

Example 6

In this example, the sample is 0.314 g of a bimetallic Pt—Pd catalyst supported on alumina with a metal loading of 2.0 wt % of Pt (Pt=102.51 µmol/g) and 1.0 wt % of Pd (Pd=93.98 µmol/g). The platinum and palladium metal species are in close contact in this sample. Steps 220 and 230 are carried out using $H_2$ as the reduction gas on the sample and $N_{chem}(H_2)$ of 59.1 µmol/g is determined. $N_{ads}(CO)$ of 61.85 µmol/g is determined separately using pulse adsorption. $\theta_H$ for this sample is 1 because $\theta_H$ for both Pt and Pd are 1, and that $\theta_{CO}$ for this sample is between $\theta_{CO}$ for Pt (1) and $\theta_{CO}$ for Pd (2). Alloys of two metals may exhibit adsorption properties different from physical mixture of two metals and thus it is not appropriate to assume here that $\theta_{CO}$ for this sample follows a linear relationship with the relative composition of Pt and Pd. Therefore, two extreme cases of $\theta_{CO}$ are examined for this sample. The first is where $\theta_{CO}=1$ and the second is where $\theta_{CO}=2$. When $\theta_{CO}=1$, y=0.48 and the oxygen content is $y*N_{chem}(H_2)$ or 28.37 µmol/g. The oxygen concentration, O/(Pt+Pd), is 14 at %. When $\theta_{CO}=2$, y=0.04 and the oxygen content is $y*N_{chem}(H_2)$ or 2.36 µmol/g giving an oxygen concentration, O/(Pt+Pd) of 1 at %. Therefore, the possible oxygen content of this sample falls in the range of 1-14 at %, which is much smaller than that in the mixed sample in Example 5. An XPS study on this bimetallic sample also suggests that Pt and Pd exist in metallic forms (i.e., $Pt^0$ and $Pd^0$).

It can be seen from Examples 5 and 6 that the method described above clearly distinguishes oxygen content between a physically mixed PtPd catalyst and a supported Pt—Pd catalyst sample having platinum and palladium metal species in close contact. The oxygen content in the physically mixed sample is more than 4 times that in the other sample. Such a determination can be used to estimate the extent of metal-metal contact between samples and aid catalyst synthesis method development. The results can also be used to correlate the catalytic reactivity with the oxygen content in the samples.

While particular embodiments according to the invention have been illustrated and described above, those skilled in the art understand that the invention can take a variety of forms and embodiments within the scope of the appended claims.

What is claimed is:

1. A method for determining the surface and bulk oxygen concentration of metal species, comprising the steps of:
   performing volumetric measurements on the metal species using a first probe gas and determining an amount of the first probe gas that has been chemically consumed by the metal species;
   heat treating the metal species;
   performing a chemisorption measurement on the treated metal species using a second probe gas and determining an amount of the second probe gas that has been chemically adsorbed onto the treated metal species; and
   determining an oxygen concentration of the metal species based on a difference between the amount of the first probe gas that has been chemically consumed by the metal species and the amount of the second probe gas that has been chemically adsorbed onto the treated metal species.

2. The method according to claim 1, further comprising the step of determining a dispersion of the treated metal species.

3. The method according to claim 2, further comprising the step of comparing the oxygen concentration with the dispersion, wherein the oxygen concentration represents the surface oxygen concentration if the oxygen concentration is less than the dispersion.

4. The method according to claim 1, wherein the step of performing volumetric measurements on the metal species includes the steps of:
   determining a total amount of the first probe gas that has been consumed by the metal species;
   determining an amount of the first probe gas that has been physically adsorbed onto the metal species; and
   determining the amount of the first probe gas that has been chemically consumed by the metal species as the difference between the total amount of the first probe gas that has been consumed by the metal species and the amount of the first probe gas that has been physically adsorbed onto the metal species.

5. The method according to claim 4, wherein the step of performing the chemisorption measurement on the treated metal species includes the step of performing a volumetric adsorption measurement on the treated metal species using the second probe gas.

6. The method according to claim 4, wherein the step of performing the chemisorption measurement on the treated metal species includes the step of performing a pulse adsorption measurement on the treated metal species using the second probe gas.

7. A method for determining oxygen content of metal species in heterogeneous catalysts, comprising the steps of:
   preparing a heterogeneous catalyst sample;
   performing volumetric measurements on the sample using a first probe gas and determining an amount of the first probe gas that has been chemically consumed by the metal species in the sample;
   heat treating the sample;
   performing a chemisorption measurement on the treated sample using a second probe gas and determining an amount of the second probe gas that has been chemically adsorbed onto the metal species in the treated sample; and
   determining an oxygen content of the metal species in the sample based on a difference between the amount of the first probe gas that has been chemically consumed by the metal species in the sample and the amount of the second probe gas that has been chemically adsorbed onto the metal species in the treated sample.

8. The method according to claim 7, wherein the step of performing volumetric adsorption measurements on the sample includes the steps of:
   determining a total amount of the first probe gas that has been consumed by the metal species in the sample;
   determining an amount of the first probe gas that has been physically adsorbed onto the metal species in the sample; and
   determining the amount of the first probe gas that has been chemically consumed by the metal species in the sample as the difference between the total amount of the first probe gas that has been consumed by the metal species in the sample and the amount of the first probe gas that has been physically adsorbed onto the metal species in the sample.

9. The method according to claim 7, wherein the step of performing the chemisorption measurement on the treated sample includes the step of performing a volumetric adsorption measurement on the treated sample using the second probe gas.

10. The method according to claim 9, wherein the second probe gas is selected from the group consisting of $H_2$, CO, $O_2$ and NO.

11. The method according to claim 7, wherein the step of performing the chemisorption measurement on the treated sample includes the step of performing a pulse adsorption measurement on the treated sample using the second probe gas.

12. The method according to claim 11, wherein the second probe gas is selected from the group consisting of $H_2$, CO, $O_2$ and NO.

13. The method according to claim 7, wherein the first probe gas and the second probe gas are the same and are selected from the group consisting of $H_2$ and CO.

14. The method according to claim 7, wherein the first probe gas and the second probe gas are different and are selected from the group consisting of $H_2$ and CO.

15. A method for determining oxygen content range of metal species in multi-metallic heterogeneous catalysts, comprising the steps of:
   preparing a heterogeneous catalyst sample;
   measuring a metal loading of each of the metal species in the sample;
   performing volumetric measurements on the sample using a first probe gas and determining an amount of the first probe gas that has been chemically consumed by the metal species in the sample;
   heat treating the sample;
   performing a chemisorption measurement on the treated sample using a second probe gas and determining an amount of the second probe gas that has been chemically adsorbed onto the metal species in the treated sample; and
   determining an oxygen content range of the metal species in the sample based on a difference between the amount of the first probe gas that has been chemically consumed by the metal species in the sample and the amount of the second probe gas that has been chemically adsorbed onto the metal species in the treated sample.

16. The method according to claim 15, wherein the step of determining an oxygen content range includes the steps of:
   determining a first oxygen content of the metal species in the sample based on a difference between the amount of the first probe gas that has been chemically consumed by the metal species in the sample, the amount of the second probe gas that has been chemically adsorbed onto the metal species in the treated sample, and a saturation adsorption coverage of the second probe gas on a first of the metal species in the treated sample; and
   determining a second oxygen content of the metal species in the sample based on a difference between the amount of the first probe gas that has been chemically consumed by the metal species in the sample, the amount of the second probe gas that has been chemically adsorbed onto the metal species in the treated sample, and a saturation adsorption coverage of the second probe gas on a second of the metal species in the treated sample,
   wherein the oxygen content range extends from the first oxygen content to the second oxygen content.

17. The method according to claim 16, wherein the first probe gas is selected from the group consisting of $H_2$ and CO, and the second probe gas is selected from the group consisting of $H_2$, CO, $O_2$ and NO.

18. The method according to claim 17, wherein the first metal species is Pt and the second metal species is Pd.

19. The method according to claim 15, wherein the step of performing volumetric measurements on the sample includes the steps of:
   determining a total amount of the first probe gas that has been consumed by the metal species in the sample;
   determining an amount of the first probe gas that has been physically adsorbed onto the metal species in the sample; and
   determining the amount of the first probe gas that has been chemically consumed by the metal species in the sample as the difference between the total amount of the first probe gas that has been consumed by the metal species in the sample and the amount of the first probe gas that has been physically adsorbed onto the metal species in the sample.

20. The method according to claim 19, wherein the step of performing the chemisorption measurement on the treated sample includes the step of performing a pulse adsorption measurement on the treated sample using the second probe gas.

21. The method according to claim 15, further comprising the steps of determining a baseline oxygen content and preparing additional quantities of the heterogeneous catalyst for further investigation using the same preparation method as the heterogeneous catalyst sample if the determined oxygen content range is substantially smaller than the baseline oxygen content.

22. The method of claim 1, wherein the first probe gas and the second probe gas are different gases.

23. The method of claim 1, wherein the first probe gas is selected from the group consisting of $H_2$ and CO.

24. The method of claim 23, wherein the second probe gas is selected from the group consisting of $H_2$, CO, $O_2$, and NO.

25. The method of claim 1, wherein the difference is determined using the following formula:

$$y = 1 - \mu \frac{N_{ads}(2^{nd} \text{ probe gas})}{N_{chem}(1^{st} \text{ probe gas})}$$

wherein:
   $N_{chem}$ is the amount of the first probe gas chemically consumed;
   $N_{ads}$ is the amount of the second probe gas chemically adsorbed;
   y is the fraction of $N_{chem}$ that reacted with oxygen; and
   $\mu$ is $(\theta_{1st\ probe\ gas}/\theta_{2nd\ probe\ gas})$, wherein $\theta$ is number of chemically adsorbed gas molecules bonded to a unit surface metal atom.

26. The method of claim 3, wherein the dispersion is determined using the following formula:

$$\text{Disperion} = \frac{N_{ads}(2^{nd} \text{ probe gas})}{\theta_{2nd\ probe\ gas} * M_{total}}$$

wherein:
   $N_{ads}$ is the amount of the second probe gas chemically adsorbed;
   $\theta_{2nd\ probe\ gas}$ is number of chemically adsorbed gas molecules bonded to a unit surface metal atom; and
   $M_{total}$ is the number of total metal atoms.

27. The method of claim 26, wherein the difference is determined using the following formula:

$$y = 1 - \mu \frac{N_{ads}(2^{nd} \text{ probe gas})}{N_{chem}(1^{st} \text{ probe gas})}$$

wherein:
   $N_{chem}$ is the amount of the first probe gas chemically consumed;
   y is the fraction of $N_{chem}$ that reacted with oxygen; and μ is ($\theta_{1st\ probe\ gas}/\theta_{2nd\ probe\ gas}$), wherein θ is number of chemically adsorbed gas molecules bonded to a unit surface metal atom.

28. The method of claim 27, wherein the first probe gas is $H_2$.

29. The method of claim 28, wherein the second probe gas is CO.

30. The method of claim 7, wherein the difference is determined using the following formula:

$$y = 1 - \mu \frac{N_{ads}(2^{nd}\ probe\ gas)}{N_{chem}(1^{st}\ probe\ gas)}$$

wherein:
- $N_{chem}$ is the amount of the first probe gas chemically consumed;
- $N_{ads}$ is the amount of the second probe gas chemically adsorbed;
- y is the fraction of $N_{chem}$ that reacted with oxygen; and
- μ is ($\theta_{1st\ probe\ gas}/\theta_{2nd\ probe\ gas}$), wherein θ is number of chemically adsorbed gas molecules bonded to a unit surface metal atom.

31. The method of claim 15, wherein the difference is determined using the following formula:

$$y = 1 - \mu \frac{N_{ads}(2^{nd}\ probe\ gas)}{N_{chem}(1^{st}\ probe\ gas)}$$

wherein:
- $N_{chem}$ is the amount of the first probe gas chemically consumed;
- $N_{ads}$ is the amount of the second probe gas chemically adsorbed;
- y is the fraction of $N_{chem}$ that reacted with oxygen; and
- μ is ($\theta_{1st\ probe\ gas}/\theta_{2nd\ probe\ gas}$), wherein θ is number of chemically adsorbed gas molecules bonded to a unit surface metal atom.

* * * * *